(12) United States Patent
Kwon et al.

(10) Patent No.: US 10,929,039 B2
(45) Date of Patent: Feb. 23, 2021

(54) DNA DIGITAL DATA STORAGE DEVICE AND METHOD, AND DECODING METHOD OF DNA DIGITAL DATA

(71) Applicants: UNIVERSITY-INDUSTRY COOPERATION GROUP OF KYUNG HEE UNIVERSITY, Yongin-si (KR); Seoul National University R&DB Foundation, Seoul (KR)

(72) Inventors: Sunghoon Kwon, Seoul (KR); Wook Park, Yongin-si (KR); Yeongjae Choi, Seoul (KR); Taehoon Ryu, Seoul (KR); Suk-Heung Song, Yongin-si (KR); Hyeli Kim, Suwon-si (KR); Seojoo Kim, Suwon-si (KR)

(73) Assignees: UNIVERSITY-INDUSTRY COOPERATION GROUP OF KYUNG HEE UNIVERSITY, Gyeongi-do (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 91 days.

(21) Appl. No.: 16/138,123

(22) Filed: Sep. 21, 2018

(65) Prior Publication Data

US 2019/0317684 A1 Oct. 17, 2019

(30) Foreign Application Priority Data

Apr. 11, 2018 (KR) .................. 10-2018-0042269

(51) Int. Cl.
*G06F 3/06* (2006.01)
*C07H 21/04* (2006.01)
*C07H 21/02* (2006.01)

(52) U.S. Cl.
CPC ........... *G06F 3/0638* (2013.01); *C07H 21/02* (2013.01); *C07H 21/04* (2013.01); *G06F 3/0604* (2013.01); *G06F 3/0673* (2013.01)

(58) Field of Classification Search
CPC .... G06F 3/0638; G06F 3/0604; G06F 3/0673; G06F 17/40; C07H 21/02; C07H 21/04; H03M 7/30; H03M 7/00
See application file for complete search history.

(56) References Cited

U.S. PATENT DOCUMENTS

2005/0053968 A1* 3/2005 Bharadwaj ............. G16B 30/00 435/6.12
2009/0270277 A1* 10/2009 Glick .................... G16B 30/00 506/24

(Continued)

FOREIGN PATENT DOCUMENTS

KR 1020150037824 A 4/2015
WO 2016059610 A1 4/2016

(Continued)

OTHER PUBLICATIONS

Andrew D. Johnson, An Extended IUPAC Nomenclature Code for Polymorphic Nucleic Acids, Bioinformatics Advanced Access, vol. 26, No. 10, 2010, pp. 1386-1389.

(Continued)

*Primary Examiner* — Hiep T Nguyen
(74) *Attorney, Agent, or Firm* — Cantor Colburn LLP

(57) ABSTRACT

Disclosed is a storage method of DNA digital data, including: encoding a plurality of bit data to a plurality of base sequences including at least one degenerate base; and synthesizing at least two types of bases constituting the at least one degenerate base on a substrate based on a mixing ratio.

15 Claims, 17 Drawing Sheets

Specification includes a Sequence Listing.

(56) References Cited

U.S. PATENT DOCUMENTS

| | | | |
|---|---|---|---|
| 2011/0099322 A1* | 4/2011 | Brownell | G16B 50/00 |
| | | | 711/103 |
| 2015/0184238 A1* | 7/2015 | Eshoo | C12Q 1/6869 |
| | | | 506/4 |
| 2015/0261664 A1* | 9/2015 | Goldman | G06F 12/023 |
| | | | 711/154 |
| 2017/0253871 A1* | 9/2017 | Bang | C12N 15/1093 |
| 2017/0338943 A1 | 11/2017 | Lu et al. | |
| 2018/0230509 A1* | 8/2018 | Chen | C12Q 1/6806 |
| 2019/0194738 A1* | 6/2019 | Chakradhar | G16B 20/00 |
| 2019/0325040 A1* | 10/2019 | Sagi | G06F 16/1748 |
| 2019/0355442 A1* | 11/2019 | Merriman | C12Q 1/6869 |
| 2019/0376120 A1* | 12/2019 | Strauss | C12Q 1/6806 |

FOREIGN PATENT DOCUMENTS

| | | |
|---|---|---|
| WO | 2016081712 A1 | 5/2016 |
| WO | 2017011492 A1 | 1/2017 |
| WO | 2017085245 A1 | 5/2017 |

OTHER PUBLICATIONS

Hwang, B. and Bang, D. Toward a new paradigm of DNA writing using a massively parallel sequencing platform and degenerate oligonucleotide. Sci. Rep. 6, 37176; doi: 10.1038/srep37176 (2016), 7 pages.

* cited by examiner

FIG. 2B

Degenerate bases

| SEQ ID NO. | G | H | G | D | B | R | A | D | C | K | G |
|---|---|---|---|---|---|---|---|---|---|---|---|
| 2 | G | A | G | G | G | A | A | A | C | T | G |
| 3 | G | C | G | T | C | G | A | G | C | G | G |
| 4 | G | T | G | G | C | A | A | T | C | G | G |
| 5 | G | T | G | A | G | G | A | G | C | T | G |
| ⋮ | | | | | | | | | | | |
| 6 | G | C | G | A | T | A | A | A | C | G | G |
| 7 | G | A | G | T | T | G | A | T | C | T | G |

| Symbol | Base mix |
|---|---|
| R | A, G |
| Y | C, T |
| M | A, C |
| K | G, T |
| S | C, G |
| W | A, T |

| Symbol | Base mix |
|---|---|
| H | A, C, T |
| B | C, G, T |
| V | A, C, G |
| D | A, G, T |
| N | A, C, G, T |

FIG. 2D

```
●  ●                        BiNEL.txt — Edited
The BiNEL (Biophotonics and Nano Engineering Lab) is located at the Seoul
National University. Professor Sunghoon Kwon's group is operated since
2006.

Current members :

Junhoi Kim, Hunjong Na, Sungsik Kim, Dong Yoon Oh, Daewon Lee, Sangwook
Bae, Yeongjae Choi, Seowoo Song, Yunjin Jeong, Okju Kim, Seohee Chang,
Sudeok Kim, Amos Chungwon Lee, Huiran Yeom, Tae Geun Lim, Hyun Yong
Jeong, Jinsung Noh, Jinhyun Kim, SeongKyu Cho, Gi Yoon Lee, Hansol Choi,
Yongju Lee, Hyunho Lee, Yonghee Lee, Wonseok Choi, Sumin Lee, Unah Kim,
Jinwoo Hyun, HongKeun Oh, Keum Hee Hwang Alumni:

Hyung Jong Bae, Jungmin Kim, Younghoon Song, Yushin Jung, Taehoon Ryu,
Jungil Choi, Dongyoung Lee, Sangkwon Han, Howon Lee, Jisung Jang, Jiyun
Kim, Jaekyung Koh, Eun Geun Kim, Saifullah Lone, Taehong Kwon, Hyoki Kim,
Su Eun Chung, Wook Park, Na Ri Kim, Sung-Eun Choi
```

NGS, Classifying by address

FIG. 3B

|  |  | SEQ ID NO. |
|---|---|---|
| Read 1 | ...G\|A\|G\|G\|A\|A\|C\|T\|G... | 2 |
| Read 2 | ...G\|C\|G\|T\|C\|G\|A\|G\|C\|G\|G... | 3 |
| Read 3 | ...G\|T\|G\|G\|C\|A\|A\|T\|C\|G\|G... | 4 |
| Read 4 | ...G\|T\|G\|A\|G\|G\|A\|G\|C\|T\|G... | 5 |
| Read 5 | ...G\|C\|G\|A\|T\|A\|A\|C\|G\|G... | 6 |
| Read 6 | ...G\|A\|G\|T\|T\|G\|A\|T\|C\|T\|G... | 7 |
| Confirmed | ...G\|H\|G\|D\|B\|R\|A\|D\|C\|K\|G... | |

Categorizing sequencing data into encoding characters

——— A, C, G, T, W, S(6) - Experiment

—‧‧— A, C, G, T, W, S(6) - Simulation

—·— A, C, G, T, R, Y, M, K, S, W, H, V, D, N(15) - Simulation

·········· A, C, G, T, [R, Y, M, K, S, W - ratio of bases mixed 3:7 and 7:3], H, V, D, N(21) - Simulation ent application No. 10-2018-0042269 filed in the Korean Intellectual Property Office on Apr. 11, 2018, the entire contents of which are incorporated herein by reference.

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
aagcagccat gcacccara                                              19

<210> SEQ ID NO 2
<211> LENGTH: 11
<212> TYPE: DNA
<213> ORGANISM: Artificial Sequence
<220> FEATURE:
<223> OTHER INFORMATION: Synthetic

<400> SEQUENCE: 2
gagggaaact g                                                      11
```

```
<210> SEQ ID NO 3
<211> LENGTH: 11
<212> TYPE: DNA
<213> ORGANISM: Artificial Sequence
<220> FEATURE:
<223> OTHER INFORMATION: Synthetic

<400> SEQUENCE: 3
gcgtcgagcg g                                                           11

<210> SEQ ID NO 4
<211> LENGTH: 11
<212> TYPE: DNA
<213> ORGANISM: Artificial Sequence
<220> FEATURE:
<223> OTHER INFORMATION: Synthetic

<400> SEQUENCE: 4
gtggcaatcg g                                                           11

<210> SEQ ID NO 5
<211> LENGTH: 11
<212> TYPE: DNA
<213> ORGANISM: Artificial Sequence
<220> FEATURE:
<223> OTHER INFORMATION: Synthetic

<400> SEQUENCE: 5
gtgaggagct g                                                           11

<210> SEQ ID NO 6
<211> LENGTH: 11
<212> TYPE: DNA
<213> ORGANISM: Artificial Sequence
<220> FEATURE:
<223> OTHER INFORMATION: Synthetic

<400> SEQUENCE: 6
gcgataaacg g                                                           11

<210> SEQ ID NO 7
<211> LENGTH: 11
<212> TYPE: DNA
<213> ORGANISM: Artificial Sequence
<220> FEATURE:
<223> OTHER INFORMATION: Synthetic

<400> SEQUENCE: 7
gagttgatct g                                                           11

<210> SEQ ID NO 8
<211> LENGTH: 11
<212> TYPE: DNA
<213> ORGANISM: Artificial Sequence
<220> FEATURE:
<223> OTHER INFORMATION: Synthetic

<400> SEQUENCE: 8
ghgdbradck g                                                           11
```

DNA DIGITAL DATA STORAGE DEVICE AND METHOD, AND DECODING METHOD OF DNA DIGITAL DATA

CROSS-REFERENCE TO RELATED APPLICATION

This application claims priority to and the benefit of Korean Patent Application No. 10-2018-0042269 filed in the Korean Intellectual Property Office on Apr. 11, 2018, the entire contents of which are incorporated herein by reference.

BACKGROUND OF THE INVENTION (a) Field of the Invention

The present disclosure relates to a storage device and a storage method of DNA digital data, and a decoding method of the DNA digital data.

(b) Description of the Related Art

The exponentially increasing rate for the annual demand for digital data storage is expected to surpass the supply of silicon in 2040, assuming that all data is stored in flash memory for instant access (1). Considering the massive accumulation of digital data in the 21st century, the development of alternative storage methods is essential.

Due to high physical information density and durability of DNA, the use of the DNA as a digital data storage medium has emerged as a method for addressing a rapidly growing demand for information storage.

However, DNA digital data storage devices are not yet actually implemented because cost per unit data storage is high.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to actually implement a storage device, a storage method, and a decoding method of DNA digital data by reducing digital data storage cost using DNA.

An exemplary embodiment of the present invention provides a storage method of DNA digital data, including: encoding a plurality of bit data to a plurality of base sequences including at least one degenerate base; and synthesizing at least two types of bases constituting the at least one degenerate base on a substrate based on a mixing ratio.

The storage method of DNA digital data may further include synthesizing a single type of base among the plurality of base sequences on the substrate.

The synthesizing of the at least one degenerate base may include incorporating the at least two types of bases based on the mixing ratio onto the substrate.

The synthesizing of the at least one degenerate base may include incorporating the at least two types of bases mixed according to the mixing ratio onto the substrate from the outside.

The ratios of the at least two types of bases may be the same in the mixing ratio.

The ratios of the at least two types of bases may be different in the mixing ratio.

The at least two types of bases may be at least one of a DNA base, an RNA base, and a nucleic acid analogue.

Another exemplary embodiment of the present invention provides a storage device of DNA digital data in which a plurality of base sequences to which a plurality of bit data is encoded is divided and stored as a basic storage unit, including: molecules in which a plurality of bases is synthesized based on a first base sequence corresponding to the basic storage unit among the plurality of base sequences, in which the first base sequence includes a first degenerate base consisting of at least two types of bases, and the molecules include first molecules in which a first base is synthesized among the at least two types of bases, and second molecules in which at least one second base is synthesized among the at least two types of bases.

Ratios between the first molecules and the second molecules may follow a mixing ratio. The ratios of the at least two types of bases may be the same or different in the mixing ratio.

The at least two types of bases may be at least one of a DNA base, an RNA base, and a nucleic acid analogue.

Yet another exemplary embodiment of the present invention provides a decoding method of DNA data, including: categorizing a plurality of DNA fragments according to an address; analyzing a base at the same position with respect to each of the plurality of categorized DNA fragments; calculating a scatter plot of a base ratio based on a result of the analysis; determining a base at a corresponding location as a degenerate base when the scatter plot of the base ratio is a mixing ratio of at least two bases; and decoding data based on the determined degenerate base.

The analyzing of the base may include analyzing base call for each location of each of the plurality of DNA fragments.

In the decoding method of DNA data, the base at the corresponding location may be determined as a first degenerate base when the scatter plot of the base ratio is a first mixing ratio of at least two bases, the base at the corresponding location may be determined as a second degenerate base when the scatter plot of the base ratio is a second mixing ratio of the at least two bases, and the first mixing ratio and the second mixing ratio may be different from each other and the first degenerate base and the second degenerate base may be different from each other.

According to exemplary embodiments of the present invention, a storage device, a storage method, and a decoding method of DNA digital data can be actually implemented by reducing digital data storage cost using DNA.

BRIEF DESCRIPTION OF THE DRAWINGS

FIGS. 2A to 2C are diagrams illustrating a storage method for DNA digital data, which compresses a DNA length by adding a degenerate base in storing a text file of FIG. 2D as a first experimental example for describing the exemplary embodiment. The sequence GHGDBRADCK G in each of FIGS. 2A, 2B, and 2C is SEQ ID NO:8 in the sequence listing.

FIGS. 3A to 3D are diagrams illustrating a storage structure and a decoding process of DNA digital data according to the first experimental example. The sequence GHGD-BRADCK G in FIG. 3B is SEQ ID NO:8.

DETAILED DESCRIPTION OF THE EMBODIMENTS

Figure 1:
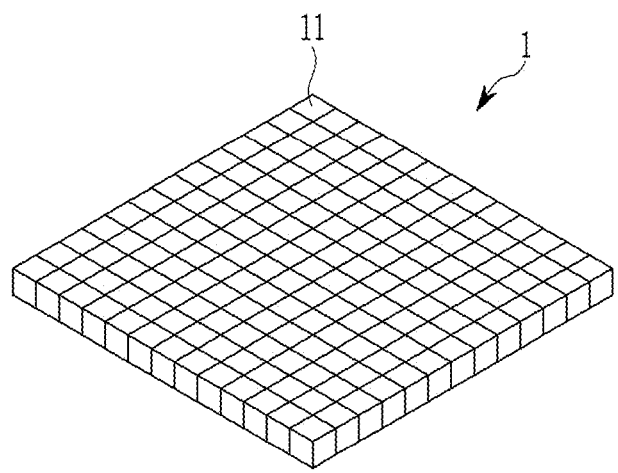
FIG. 1 is a diagram illustrating one example a storage device of DNA digital data according to an exemplary embodiment.

Hereinafter, the present invention will be described in detail so as to be easily implemented by those skilled in the art, with reference to the accompanying drawings. However, the present invention is not limited to the description in the present disclosure and may be embodied in other forms.

The present disclosure relates to a device for encoding data with DNA and a method thereof using sequences of degenerate bases or mixed bases indicating additional characters other than adenine (A), cytosine (C), guanine (G), and thymine (T) in order to compress a length of DNA required to store corresponding data. Then, a digital data storage device using the DNA (hereinafter, referred to as a DNA digital data storage device) may be actually provided by reducing data storage cost using the DNA.

The use of the DNA as a digital data storage medium has two major advantages. The two major advantages are a high physical information density capable of storing petabytes of data per gram of DNA and durability that lasts for centuries without energy input.

A major goal of previous research on DNA digital data storage is to improve a data encoding algorithm for reducing a data error or loss. For example, an algorithm has been proposed, which removes a high GC content and a long homopolymer in the encoding, which are known to cause an error. In addition, various error correction algorithms for the DNA digital data storage have been developed to correct errors or recover deleted data fragments during decoding. Previous studies on such an encoding algorithm have accelerated a potential of the DNA as the digital data storage medium by eliminating almost all data errors or losses.

A next step toward ideal DNA digital data storage is to reduce data storage cost. According to the previous studies, only when DNA cost is reduced to approximately 1/100, the DNA may be put to practical use as a back-up storage medium. Therefore, the cost should be minimized by increasing an amount (information capacity, bit/nt) of data that may be stored per synthesized nucleotide and compressing the DNA length for data storage. However, since the previous DNA digital data storage uses four types of characters (A, C, G, and T) for bit encoding, the previous DNA digital data storage has its theoretical limit in information density of log 24, or 2.0 bit/nt. Since the previous research has almost reached a theoretical upper limit, the information capacity does not increase much unless additional encoding characters are introduced.

In an exemplary embodiment, degenerate bases or mixed bases associated with combinations based on four DNA bases are used as additional characters for encoding beyond an information capacity limit of 2.0 bit/nt. In the exemplary embodiment, the degenerate base may produce numerous variations at a single base position without additional cost.

In the exemplary embodiment, when bases stored in one position of a DNA digital data storage device are sequenced so that when two types or more base sequences are read, a base combination at that position is detected as the degenerate base and determined to correspond to encoding characters other than A, C, G, and T. For example, using a total of 15 encoding characters, including A, C, G, and T, the information capacity is improved to 3.37 bit/nt and the DNA length required to store the same data is compressed by half as compared with the related art. Then, the cost of storing the DNA digital data may be reduced by more than half.

FIG. 1 is a diagram illustrating one example of a DNA digital data storage device according to an exemplary embodiment.

As illustrated in FIG. 1, the DNA digital data storage device 1 includes a plurality of memory cells 11. In FIG. 1, it is illustrated that a plurality of memory cells 11 is arranged in a matrix form, but the present invention is not limited thereto. The memory cell may be implemented as a tube and in this case, the DNA digital data storage device 1 may include a plurality of tubes and an arrangement form is not limited.

Molecules formed by synthesizing a plurality of base sequences corresponding to one fragment which is a basic storage unit may be stored in each of the plurality of memory cells 11.

Figure 2A:
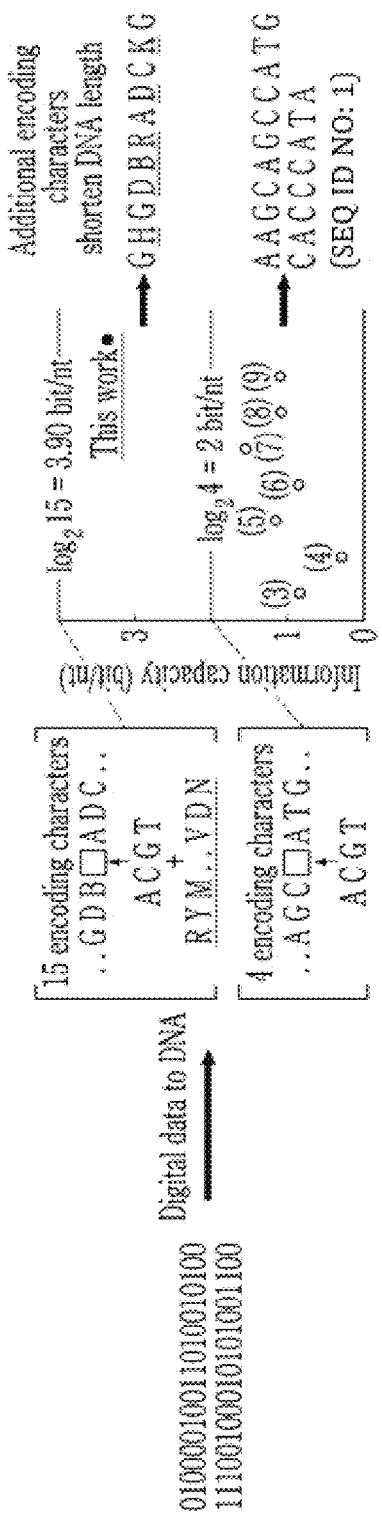
Figure 2C:
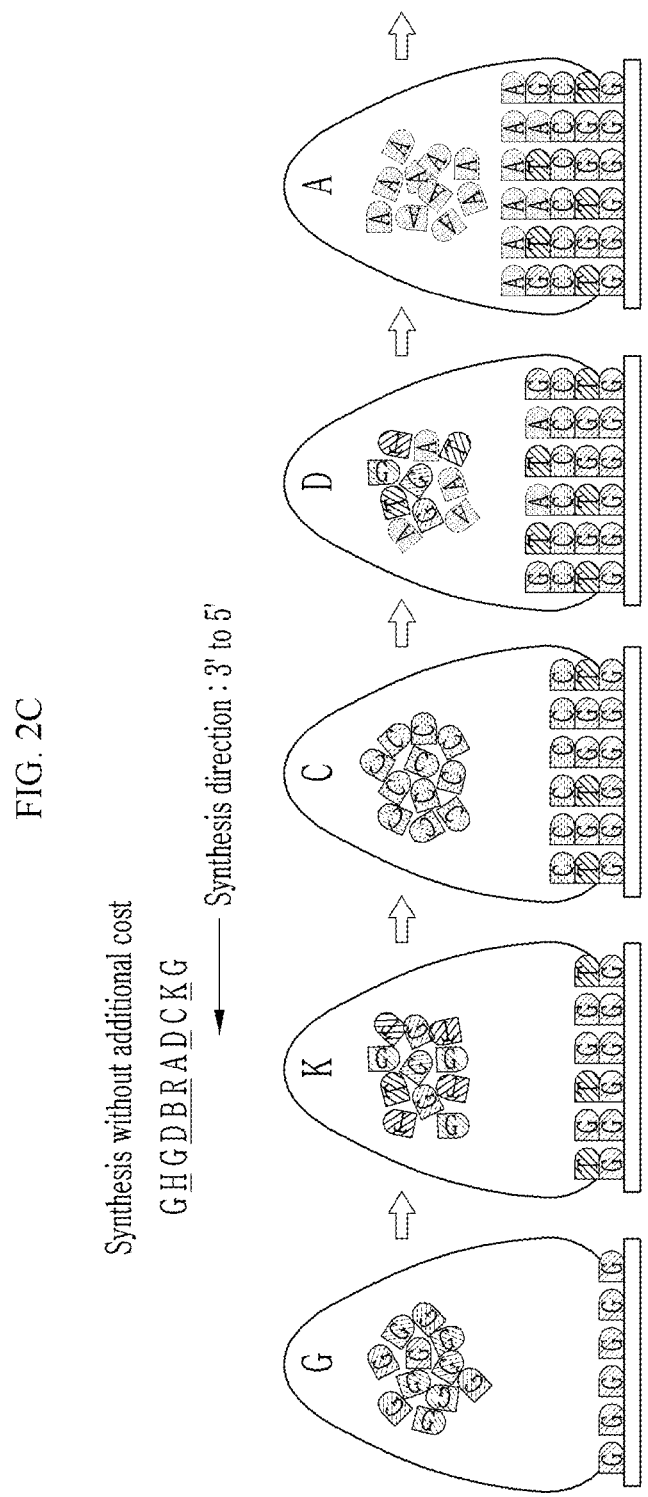

FIGS. 2A to 2C are diagrams illustrating storing of DNA digital data, which compresses a DNA length by adding a degenerate base as a first experimental example for describing the exemplary embodiment.

As illustrated in FIG. 2B, in addition to A, C, G, and T, 11 kinds of degenerate bases may be used to encode digital data into the DNA. Then, this conversion from four to fifteen characters-based encoding system theoretically allows maximum information capacity of 3.90 bit/nt ($\log_2 15$) from previous 2.0 bit/nt ($\log_2 4$). The binary data may be encoded into a DNA sequence corresponding to a total of 15 encoding characters consisting of A, C, G, T and 11 additional degenerate bases.

The length of the DNA encoded according to a first experimental example is smaller than the length of the encoding method in the related art, which uses only A, C, G, and T because there are the added encoding characters. For example, as illustrated in FIG. 2A, in the exemplary embodiment, 40 bits may be encoded as 11 nt, which is denoted as "This work". It can be seen that the information capacity according to the first experimental example is approximately twice higher than that of cases (3) to (9) of encoding 40 bits according to encoding methods in the related art.

The degenerate base represents an additional character configured by a mixed pool of nucleotides. The degenerative part of the encoded sequence is incorporated by mixing the DNA phosphoramidites during the synthesis procedure. As illustrated in FIG. 2C, the base 'A' is synthesized on a substrate according to a synthesis order of 3' to 5', and the bases 'T' and 'G' constituting the degenerate base X' are synthesized on the basis of a mixing ratio, the base 'C' is synthesized, and each of 'A', 'G', and 'T' constituting the degenerate base 'D is synthesized based on the mixing ratio. In FIG. 2B, bases constituting the degenerate base are incorporated into the substrate based on the mixing ratio. However, the present invention is not limited thereto. The bases constituting the degenerate base may be mixed according to the mixing ratio in other device and thereafter, the mixed bases may be incorporated into the substrate.

FIG. 2C illustrates a result of synthesizing a plurality of base sequences corresponding to one fragment which is the basic storage unit in one column on the substrate (column method). However, the method in which the plurality of base sequences is synthesized is not limited thereto and synthesis may be performed on a glass substrate according to an inkjet method (inkjet method). Since a total amount of phosphoramidite used is the same in column-based and inkjet-based oligonucleotide synthesis, the degenerate base may be encoded with no additional cost. Therefore, in the exemplary embodiment, when the same amount of data is stored, the length of the DNA may be shorted to approximately half of the length of the DNA in the related art at the same unit synthesis cost, thereby reducing data storage cost.

In the first experimental example, an 854-byte text file illustrated in FIG. 2D is encoded into the DNA sequence.

FIG. 2D illustrates one example of the text file for the first experimental example.

The data may be transformed into a series of DNA codons and the codon may be constituted by three of 15 characters. In order to avoid a homopolymer of 4 bases or more, a last position sequence of the codon and a front sequence of the codon should not be the same.

Table 1 below shows the codon constituted by 3 characters out of 15 characters.

TABLE 1

| | | | | | |
|---|---|---|---|---|---|
| ACA | ZTA | OYA | USA | DIA | BXA |
| CCA | XTA | PYA | ISA | NIA | VXA |
| TCA | AGA | ZYA | OSA | UIA | DXA |
| GCA | CGA | XYA | PSA | IIA | NXA |
| RCA | TGA | AKA | ZSA | OIA | UXA |
| YCA | GGA | CKA | XSA | PIA | IXA |
| MCA | RGA | TKA | ABA | ZIA | OXA |
| KCA | YGA | GKA | CBA | XIA | PXA |
| WCA | MGA | RKA | TBA | APA | ZXA |
| SCA | KGA | YKA | GBA | CPA | XXA |
| HCA | WGA | MKA | RBA | TPA | AAC |
| BCA | SGA | KKA | YBA | GPA | CAC |
| VCA | HGA | WKA | MBA | RPA | TAC |
| DCA | BGA | SKA | KBA | YPA | GAC |
| NCA | VGA | HKA | WBA | MPA | RAC |
| UCA | DGA | BKA | SBA | KPA | YAC |
| ICA | NGA | VKA | HBA | WPA | MAC |
| OCA | UGA | DKA | BBA | SPA | KAC |
| PCA | IGA | NKA | VBA | HPA | WAC |
| ZCA | OGA | UKA | DBA | BPA | SAC |
| XCA | PGA | IKA | NBA | VPA | HAC |
| ATA | ZGA | OKA | UBA | DPA | BAC |
| CTA | XGA | PKA | IBA | NPA | VAC |
| TTA | AYA | ZKA | OBA | UPA | DAC |
| GTA | CYA | XKA | PBA | IPA | NAC |
| RTA | TYA | ASA | ZBA | OPA | UAC |
| YTA | GYA | CSA | XBA | PPA | IAC |
| MTA | RYA | TSA | AIA | ZPA | OAC |
| KTA | YYA | GSA | CIA | XPA | PAC |
| WTA | MYA | RSA | TIA | AXA | ZAC |
| STA | KYA | YSA | GIA | CXA | XAC |
| HTA | WYA | MSA | RIA | TXA | ATC |
| BTA | SYA | KSA | YIA | GXA | CTC |
| VTA | HYA | WSA | MIA | RXA | TTC |
| DTA | BYA | SSA | KIA | YXA | GTC |
| NTA | VYA | HSA | WIA | MXA | RTC |
| UTA | DYA | BSA | SIA | KXA | YTC |
| ITA | NYA | VSA | HIA | WXA | MTC |
| OTA | UYA | DSA | BIA | SXA | KTC |
| PTA | IYA | NSA | VIA | HXA | WTC |
| STC | KRC | YWC | GUC | CZC | XAT |
| HTC | WRC | MWC | RUC | TZC | ACT |
| BTC | SRC | KWC | YUC | GZC | CCT |
| VTC | HRC | WWC | MUC | RZC | TCT |
| DTC | BRC | SWC | KUC | YZC | GCT |
| NTC | VRC | HWC | WUC | MZC | RCT |
| UTC | DRC | BWC | SUC | KZC | YCT |
| ITC | NRC | VWC | HUC | WZC | MCT |
| OTC | URC | DWC | BUC | SZC | KCT |
| PTC | IRC | NWC | VUC | HZC | WCT |
| ZTC | ORC | UWC | DUC | BZC | SCT |
| XTC | PRC | IWC | NUC | VZC | HCT |
| AGC | ZRC | OWC | UUC | DZC | BCT |
| CGC | XRC | PWC | IUC | NZC | VCT |
| TGC | AKC | ZWC | OUC | UZC | DCT |
| GGC | CKC | XWC | PUC | IZC | NCT |
| RGC | TKC | ADC | ZUC | OZC | UCT |
| YGC | GKC | CDC | XUC | PZC | ICT |
| MGC | RKC | TDC | APC | ZZC | OCT |
| KGC | YKC | GDC | CPC | XZC | PCT |
| WGC | MKC | RDC | TPC | AAT | ZCT |
| SGC | KKC | YDC | GPC | CAT | XCT |
| HGC | WKC | MDC | RPC | TAT | AGT |
| BGC | SKC | KDC | YPC | GAT | CGT |
| VGC | HKC | WDC | MPC | RAT | TGT |
| DGC | BKC | SDC | KPC | YAT | GGT |
| NGC | VKC | HDC | WPC | MAT | RGT |
| UGC | DKC | BDC | SPC | KAT | YGT |
| IGC | NKC | VDC | HPC | WAT | MGT |
| OGC | UKC | DDC | BPC | SAT | KGT |
| PGC | IKC | NDC | VPC | HAT | WGT |
| ZGC | OKC | UDC | DPC | BAT | SGT |
| XGC | PKC | IDC | NPC | VAT | HGT |
| ARC | ZKC | ODC | UPC | DAT | BGT |
| CRC | XKC | PDC | IPC | NAT | VGT |
| TRC | AWC | ZDC | OPC | UAT | DGT |
| GRC | CWC | XDC | PPC | IAT | NGT |
| RRC | TWC | AUC | ZPC | OAT | UGT |
| YRC | GWC | CUC | XPC | PAT | IGT |
| MRC | RWC | TUC | AZC | ZAT | OGT |
| PGT | IMT | NVT | VOT | HAG | WTG |
| ZGT | OMT | UVT | DOT | BAG | STG |
| XGT | PMT | IVT | NOT | VAG | HTG |
| ART | ZMT | OVT | UOT | DAG | BTG |
| CRT | XMT | PVT | IOT | NAG | VTG |
| TRT | AST | ZVT | OOT | UAG | DTG |
| GRT | CST | XVT | POT | IAG | NTG |
| RRT | TST | AUT | ZOT | OAG | UTG |
| YRT | GST | CUT | XOT | PAG | ITG |
| MRT | RST | TUT | AXT | ZAG | OTG |
| KRT | YST | GUT | CXT | XAG | PTG |
| WRT | MST | RUT | TXT | ACG | ZTG |
| SRT | KST | YUT | GXT | CCG | XTG |
| HRT | WST | MUT | RXT | TCG | AYG |
| BRT | SST | KUT | YXT | GCG | CYG |
| VRT | HST | WUT | MXT | RCG | TYG |
| DRT | BST | SUT | KXT | YCG | GYG |
| NRT | VST | HUT | WXT | MCG | RYG |
| URT | DST | BUT | SXT | KCG | YYG |
| IRT | NST | VUT | HXT | WCG | MYG |
| ORT | UST | DUT | BXT | SCG | KYG |
| PRT | IST | NUT | VXT | HCG | WYG |
| ZRT | OST | UUT | DXT | BCG | SYG |
| XRT | PST | IUT | NXT | VCG | HYG |
| AMT | ZST | OUT | UXT | DCG | BYG |
| CMT | XST | PUT | IXT | NCG | VYG |
| TMT | AVT | ZUT | OXT | UCG | DYG |
| GMT | CVT | XUT | PXT | ICG | NYG |
| RMT | TVT | AOT | ZXT | OCG | UYG |
| YMT | GVT | COT | XXT | PCG | IYG |
| MMT | RVT | TOT | AAG | ZCG | OYG |
| KMT | YVT | GOT | CAG | XCG | PYG |
| WMT | MVT | ROT | TAG | ATG | ZYG |
| SMT | KVT | YOT | GAG | CTG | XYG |
| HMT | WVT | MOT | RAG | TTG | AMG |
| BMT | SVT | KOT | YAG | GTG | CMG |
| VMT | HVT | WOT | MAG | RTG | TMG |
| DMT | BVT | SOT | KAG | YTG | GMG |
| NMT | VVT | HOT | WAG | MTG | RMG |
| UMT | DVT | BOT | SAG | KTG | YMG |
| MMG | RHG | TOG | ACR | ZTR | OIR |
| KMG | YHG | GOG | CCR | XTR | PIR |
| WMG | MHG | ROG | TCR | AYR | ZIR |
| SMG | KHG | YOG | GCR | CYR | XIR |
| HMG | WHG | MOG | RCR | TYR | AAY |
| BMG | SHG | KOG | YCR | GYR | CAY |
| VMG | HHG | WOG | MCR | RYR | TAY |

TABLE 1-continued

| | | | | | | | | | | | |
|---|---|---|---|---|---|---|---|---|---|---|---|
| DMG | BHG | SOG | KCR | YYR | GAY | HGW | WXW | MTS | RZS | TAB | ACD |
| NMG | VHG | HOG | WCR | MYR | RAY | BGW | SXW | KTS | YZS | GAB | CCD |
| UMG | DHG | BOG | SCR | KYR | YAY | VGW | HXW | WTS | MZS | RAB | TCD |
| IMG | NHG | VOG | HCR | WYR | MAY | DGW | BXW | STS | KZS | YAB | GCD |
| OMG | UHG | DOG | BCR | SYR | KAY | NGW | VXW | HTS | WZS | MAB | RCD |
| PMG | IHG | NOG | VCR | HYR | WAY | UGW | DXW | BTS | SZS | KAB | YCD |
| ZMG | OHG | UOG | DCR | BYR | SAY | IGW | NXW | VTS | HZS | WAB | MCD |
| XMG | PHG | IOG | NCR | VYR | HAY | OGW | UXW | DTS | BZS | SAB | KCD |
| AWG | ZHG | OOG | UCR | DYR | BAY | PGW | IXW | NTS | VZS | HAB | WCD |
| CWG | XHG | POG | ICR | NYR | VAY | ZGW | OXW | UTS | DZS | BAB | SCD |
| TWG | AIG | ZOG | OCR | UYR | DAY | XGW | PXW | ITS | NZS | VAB | HCD |
| GWG | CIG | XOG | PCR | IYR | NAY | ASW | ZXW | OTS | UZS | DAB | BCD |
| RWG | TIG | AZG | ZCR | OYR | UAY | CSW | XXW | PTS | IZS | NAB | VCD |
| YWG | GIG | CZG | XCR | PYR | IAY | TSW | AAS | ZTS | OZS | UAB | DCD |
| MWG | RIG | TZG | ATR | ZYR | OAY | GSW | CAS | XTS | PZS | IAB | NCD |
| KWG | YIG | GZG | CTR | XYR | PAY | RSW | TAS | AWS | ZZS | OAB | UCD |
| WWG | MIG | RZG | TTR | AIR | ZAY | YSW | GAS | CWS | XZS | PAB | ICD |
| SWG | KIG | YZG | GTR | CIR | XAY | MSW | RAS | TWS | AGH | ZAB | OCD |
| HWG | WIG | MZG | RTR | TIR | AGY | KSW | YAS | GWS | CGH | XAB | PCD |
| BWG | SIG | KZG | YTR | GIR | CGY | WSW | MAS | RWS | TGH | ATV | ZCD |
| VWG | HIG | WZG | MTR | RIR | TGY | SSW | KAS | YWS | GGH | CTV | XCD |
| DWG | BIG | SZG | KTR | YIR | GGY | HSW | WAS | MWS | RGH | TTV | ACU |
| NWG | VIG | HZG | WTR | MIR | RGY | BSW | SAS | KWS | YGH | GTV | CCU |
| UWG | DIG | BZG | STR | KIR | YGY | VSW | HAS | WWS | MGH | RTV | TCU |
| IWG | NIG | VZG | HTR | WIR | MGY | DSW | BAS | SWS | KGH | YTV | GCU |
| OWG | UIG | DZG | BTR | SIR | KGY | NSW | VAS | HWS | WGH | MTV | RCU |
| PWG | IIG | NZG | VTR | HIR | WGY | USW | DAS | BWS | SGH | KTV | YCU |
| ZWG | OIG | UZG | DTR | BIR | SGY | ISW | NAS | VWS | HGH | WTV | MCU |
| XWG | PIG | IZG | NTR | VIR | HGY | OSW | UAS | DWS | BGH | STV | KCU |
| AHG | ZIG | OZG | UTR | DIR | BGY | PSW | IAS | NWS | VGH | HTV | WCU |
| CHG | XIG | PZG | ITR | NIR | VGY | ZSW | OAS | UWS | DGH | BTV | SCU |
| THG | AOG | ZZG | OTR | UIR | DGY | XSW | PAS | IWS | NGH | VTV | HCU |
| GHG | COG | XZG | PTR | IIR | NGY | AXW | ZAS | OWS | UGH | DTV | BCU |
| UGY | DUY | BGM | SPM | KCK | YOK | VCU | HYU | WAI | MRI | RTO | TKO |
| IGY | NUY | VGM | HPM | WCK | MOK | DCU | BYU | SAI | KRI | YTO | GKO |
| OGY | UUY | DGM | BPM | SCK | KOK | NCU | VYU | HAI | WRI | MTO | RKO |
| PGY | IUY | NGM | VPM | HCK | WOK | UCU | DYU | BAI | SRI | KTO | YKO |
| ZGY | OUY | UGM | DPM | BCK | SOK | ICU | NYU | VAI | HRI | WTO | MKO |
| XGY | PUY | IGM | NPM | VCK | HOK | OCU | UYU | DAI | BRI | STO | KKO |
| ARY | ZUY | OGM | UPM | DCK | BOK | PCU | IYU | NAI | VRI | HTO | WKO |
| CRY | XUY | PGM | IPM | NCK | VOK | ZCU | OYU | UAI | DRI | BTO | SKO |
| TRY | ATM | ZGM | OPM | UCK | DOK | XCU | PYU | IAI | NRI | VTO | HKO |
| GRY | CTM | XGM | PPM | ICK | NOK | ATU | ZYU | OAI | URI | DTO | BKO |
| RRY | TTM | AKM | ZPM | OCK | UOK | CTU | XYU | PAI | IRI | NTO | VKO |
| YRY | GTM | CKM | XPM | PCK | IOK | TTU | AIU | ZAI | ORI | UTO | DKO |
| MRY | RTM | TKM | AAK | ZCK | OOK | GTU | CIU | XAI | PRI | ITO | NKO |
| KRY | YTM | GKM | CAK | XCK | POK | RTU | TIU | AGI | ZRI | OTO | UKO |
| WRY | MTM | RKM | TAK | AMK | ZOK | YTU | GIU | CGI | XRI | PTO | IKO |
| SRY | KTM | YKM | GAK | CMK | XOK | MTU | RIU | TGI | AUI | ZTO | OKO |
| HRY | WTM | MKM | RAK | TMK | ACW | KTU | YIU | GGI | CUI | XTO | PKO |
| BRY | STM | KKM | YAK | GMK | CCW | WTU | MIU | RGI | TUI | AGO | ZKO |
| VRY | HTM | WKM | MAK | RMK | TCW | STU | KIU | YGI | GUI | CGO | XKO |
| DRY | BTM | SKM | KAK | YMK | GCW | HTU | WIU | MGI | RUI | TGO | APO |
| NRY | VTM | HKM | WAK | MMK | RCW | BTU | SIU | KGI | YUI | GGO | CPO |
| URY | DTM | BKM | SAK | KMK | YCW | VTU | HIU | WGI | MUI | RGO | TPO |
| IRY | NTM | VKM | HAK | WMK | MCW | DTU | BIU | SGI | KUI | YGO | GPO |
| ORY | UTM | DKM | BAK | SMK | KCW | NTU | VIU | HGI | WUI | MGO | RPO |
| PRY | ITM | NKM | VAK | HMK | WCW | UTU | DIU | BGI | SUI | KGO | YPO |
| ZRY | OTM | UKM | DAK | BMK | SCW | ITU | NIU | VGI | HUI | WGO | MPO |
| XRY | PTM | IKM | NAK | VMK | HCW | OTU | UIU | DGI | BUI | SGO | KPO |
| AUY | ZTM | OKM | UAK | DMK | BCW | PTU | IIU | NGI | VUI | HGO | WPO |
| CUY | XTM | PKM | IAK | NMK | VCW | ZTU | OIU | UGI | DUI | BGO | SPO |
| TUY | AGM | ZKM | OAK | UMK | DCW | XTU | PIU | IGI | NUI | VGO | HPO |
| GUY | CGM | XKM | PAK | IMK | NCW | AYU | ZIU | OGI | UUI | DGO | BPO |
| RUY | TGM | APM | ZAK | OMK | UCW | CYU | XIU | PGI | IUI | NGO | VPO |
| YUY | GGM | CPM | XAK | PMK | ICW | TYU | AAI | ZGI | OUI | UGO | DPO |
| MUY | RGM | TPM | ACK | ZMK | OCW | GYU | CAI | XGI | PUI | IGO | NPO |
| KUY | YGM | GPM | CCK | XMK | PCW | RYU | TAI | ARI | ZUI | OGO | UPO |
| WUY | MGM | RPM | TCK | AOK | ZCW | YYU | GAI | CRI | XUI | PGO | IPO |
| SUY | KGM | YPM | GCK | COK | XCW | MYU | RAI | TRI | ATO | ZGO | OPO |
| HUY | WGM | MPM | RCK | TOK | AGW | KYU | YAI | GRI | CTO | XGO | PPO |
| BUY | SGM | KPM | YCK | GOK | CGW | WYU | MAI | RRI | TTO | AKO | ZPO |
| VUY | HGM | WPM | MCK | ROK | TGW | SYU | KAI | YRI | GTO | CKO | XPO |
| GGW | CXW | XAS | PWS | IGH | NTV | AAP | ZCP | OOP | UGZ | DXZ | BTX |
| RGW | TXW | ATS | ZWS | OGH | UTV | CAP | XCP | POP | IGZ | NXZ | VTX |
| YGW | GXW | CTS | XWS | PGH | ITV | TAP | AMP | ZOP | OGZ | UXZ | DTX |
| MGW | RXW | TTS | AZS | ZGH | OTV | GAP | CMP | XOP | PGZ | IXZ | NTX |
| KGW | YXW | GTS | CZS | XGH | PTV | RAP | TMP | ACZ | ZGZ | OXZ | UTX |
| WGW | MXW | RTS | TZS | AAB | ZTV | YAP | GMP | CCZ | XGZ | PXZ | ITX |
| SGW | KXW | YTS | GZS | CAB | XTV | MAP | RMP | TCZ | ASZ | ZXZ | OTX |

TABLE 1-continued

| | | | | | |
|---|---|---|---|---|---|
| KAP | YMP | GCZ | CSZ | XXZ | PTX |
| WAP | MMP | RCZ | TSZ | AAX | ZTX |
| SAP | KMP | YCZ | GSZ | CAX | XTX |
| HAP | WMP | MCZ | RSZ | TAX | AWX |
| BAP | SMP | KCZ | YSZ | GAX | CWX |
| VAP | HMP | WCZ | MSZ | RAX | TWX |
| DAP | BMP | SCZ | KSZ | YAX | GWX |
| NAP | VMP | HCZ | WSZ | MAX | RWX |
| UAP | DMP | BCZ | SSZ | KAX | YWX |
| IAP | NMP | VCZ | HSZ | WAX | MWX |
| OAP | UMP | DCZ | BSZ | SAX | KWX |
| PAP | IMP | NCZ | VSZ | HAX | WWX |
| ZAP | OMP | UCZ | DSZ | BAX | SWX |
| XAP | PMP | ICZ | NSZ | VAX | HWX |
| ACP | ZMP | OCZ | USZ | DAX | BWX |
| CCP | XMP | PCZ | ISZ | NAX | VWX |
| TCP | AOP | ZCZ | OSZ | UAX | DWX |
| GCP | COP | XCZ | PSZ | IAX | NWX |
| RCP | TOP | AGZ | ZSZ | OAX | UWX |
| YCP | GOP | CGZ | XSZ | PAX | IWX |
| MCP | ROP | TGZ | AXZ | ZAX | OWX |
| KCP | YOP | GGZ | CXZ | XAX | PWX |
| WCP | MOP | RGZ | TXZ | ATX | ZWX |
| SCP | KOP | YGZ | GXZ | CTX | XWX |
| HCP | WOP | MGZ | RXZ | TTX | AZX |
| BCP | SOP | KGZ | YXZ | GTX | CZX |
| VCP | HOP | WGZ | MXZ | RTX | TZX |
| DCP | BOP | SGZ | KXZ | YTX | GZX |
| NCP | VOP | HGZ | WXZ | MTX | RZX |
| UCP | DOP | BGZ | SXZ | KTX | YZX |
| ICP | NOP | VGZ | HXZ | WTX | MZX |
| OCP | UOP | DGZ | BXZ | STX | KZX |
| PCP | IOP | NGZ | VXZ | HTX | WZX |
| SZX | BZX | DZX | UZX | OZX | ZZX |
| HZX | VZX | NZX | IZX | PZX | XZX |

FIGS. 3A to 3D are diagrams illustrating a storage structure and a decoding process of DNA digital data according to the first experimental example.

Figure 3A:
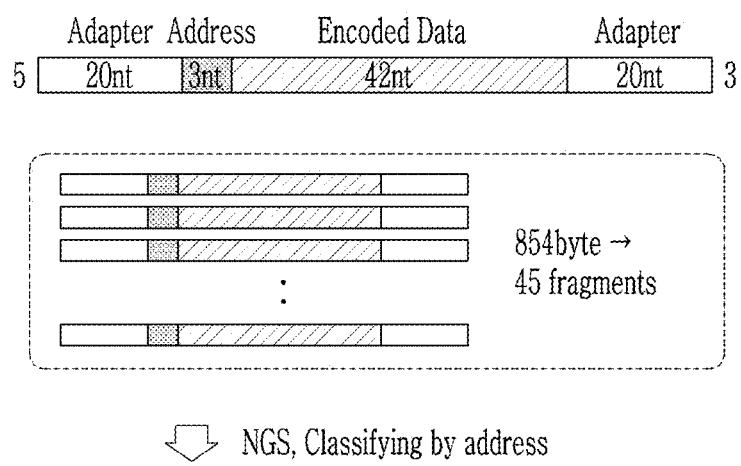
Figure 3C:
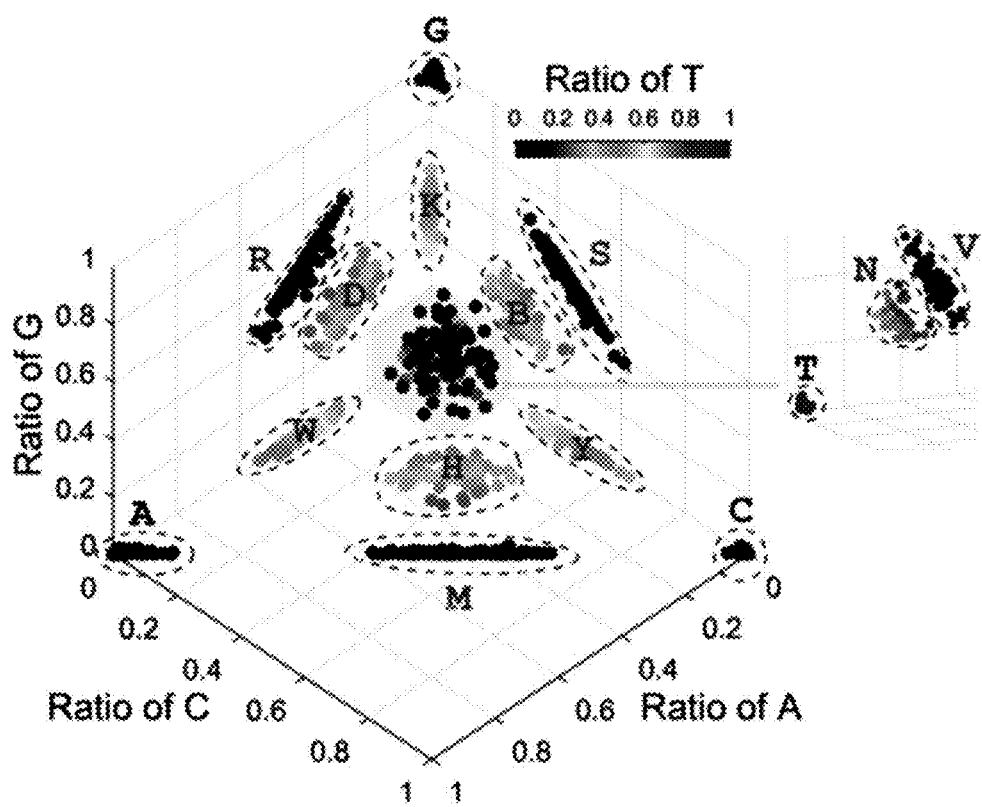
Figure 3D:
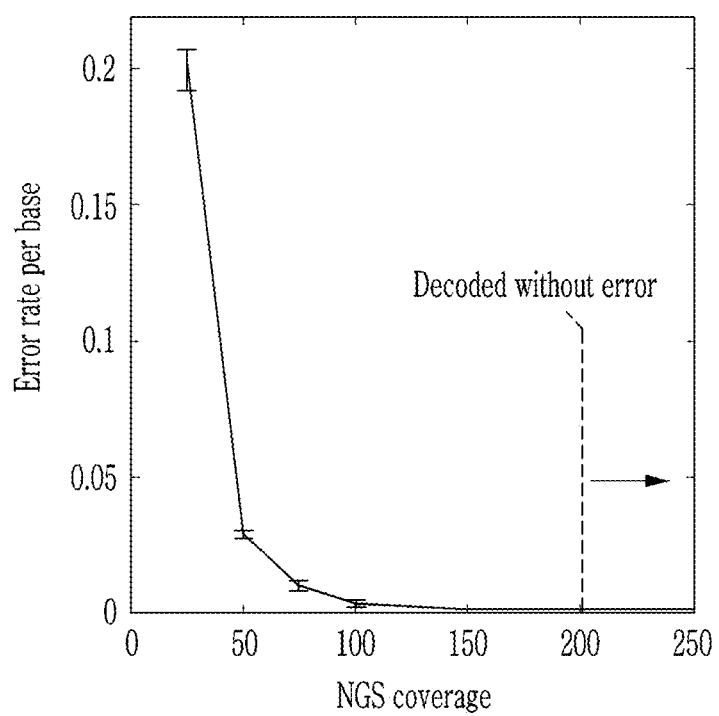

FIG. 3A illustrates a design structure of a DNA fragment and FIG. 3B illustrates that the DNA fragment is analyzed by next generation sequencing (NGS). After categorization according to an address, a character distribution based on the DNA base at the same position in each column of the DNA digital data device may be analyzed and the degenerate base may be decoded according to the determination. For example, as illustrated in FIG. 3C, the base at the same position may be analyzed, a scatter plot of a base ratio may be calculated based on the result of the analysis, and a degenerate base may be determined according to the scatter plot of the base ratio. In FIG. 3D, an error rate of determined DNA bases in specific average coverage over the total fragments is illustrated. In the graph of FIG. 3D, standard deviations (s.d.) are obtained by repeating random sampling five times and an error bar indicates s.d.

As illustrated in FIG. 3A, the encoded information is divided into fragments of 42 nt and an address constituted by bases of 3 nt is allocated. The base of 3 nt indicating the address does not include the degenerate base and an example thereof is shown in Table 2 below.

TABLE 2

| | |
|---|---|
| 1 | ACA |
| 2 | CCA |
| 3 | TCA |
| 4 | GCA |
| 5 | ATA |
| 6 | CTA |
| 7 | TTA |
| 8 | GTA |
| 9 | AGA |

TABLE 2-continued

| | |
|---|---|
| 10 | CGA |
| 11 | TGA |
| 12 | GGA |
| 13 | AAC |
| 14 | CAC |
| 15 | TAC |
| 16 | GAC |
| 17 | ATC |
| 18 | CTC |
| 19 | TTC |
| 20 | GTC |
| 21 | AGC |
| 22 | CGC |
| 23 | TGC |
| 24 | GGC |
| 25 | AAT |
| 26 | CAT |
| 27 | TAT |
| 28 | GAT |
| 29 | ACT |
| 30 | CCT |
| 31 | TCT |
| 32 | GCT |
| 33 | AGT |
| 34 | CGT |
| 35 | TGT |
| 36 | GGT |
| 37 | AAG |
| 38 | CAG |
| 39 | TAG |
| 40 | GAG |
| 41 | ACG |
| 42 | CCG |
| 43 | TCG |
| 44 | GCG |
| 45 | ATG |
| 46 | CTG |
| 47 | TTG |
| 48 | GTG |

Each fragment is supplemented with two adapters (20 nt at each of the 5' and 3' ends) for amplification and sequencing, and the total fragment length is 85 nt. In the first experimental example, 45 DNA fragments are synthesized by a column-based oligonucleotide synthesizer. Considering the number of bits encoded in the entire nucleotide synthesis except for the adapter, an information capacity of 3.37 bits/nt may be achieved in the first experimental example. A synthetic DNA library consisting of 800 molecules on average may be amplified by a designed adapter and sequenced by "Illumina MiniSeq".

Raw NGS data is filtered by a designed length and categorized for each address. As illustrated in FIG. 3B, Then, the duplicated reads are removed and the base calls of each position on the fragment are analyzed. The intermediate ratio of nucleotides analyzed is not consistently equivalent because the coupling efficiency during synthesis varies for each base both by type and position in the growing oligonucleotide.

However, when a ratio of A:C:G:T in the sequence analyzed at the same position is observed with the scatter plot, the entire distribution is divided into 15 clusters as illustrated in FIG. 3C and 11 clusters consisting of the intermediate ratio of more than two bases are considered as degenerate base. 4 remaining clusters with a dominant ratio of the specific nucleotide are considered as a pure base sequence. As described, in the first experimental example, original data may be successfully recovered from the original NGS data.

In FIG. 3D, it may be seen that data may be recovered in 10 cases out of 10 random down-sampling the average coverage to coverage of 250×. 1× coverage means reading data by detecting the type of DNA with NGS for all designed DNAs. In the raw NGS data (for example, 3600× coverage), 250× coverage is randomly downsampled and compared with the encoded original data, and as a result, there is no error in all 10 downsampling cases in which the downsampling are repeated 10 times. If the average NGS coverage is lower than 200×, the error rate increases because the intersections between the clusters of encoding characters are augmented.

Figure 4:
FIG. 4 is a thumbnail image of a Hunminjeongeum copy.

FIG. 4 is a thumbnail image of a Hunminjeongeum copy.

In order to illustrate the scalability of a DNA digital data storage platform according to the exemplary embodiment, in a second experimental example, by using a pooled oligonucleotide synthesis method, 135.4 Kbytes which is thumbnail image data of the Hunminjeongeum copy is stored in 4503 DNA fragments.

Figure 5:
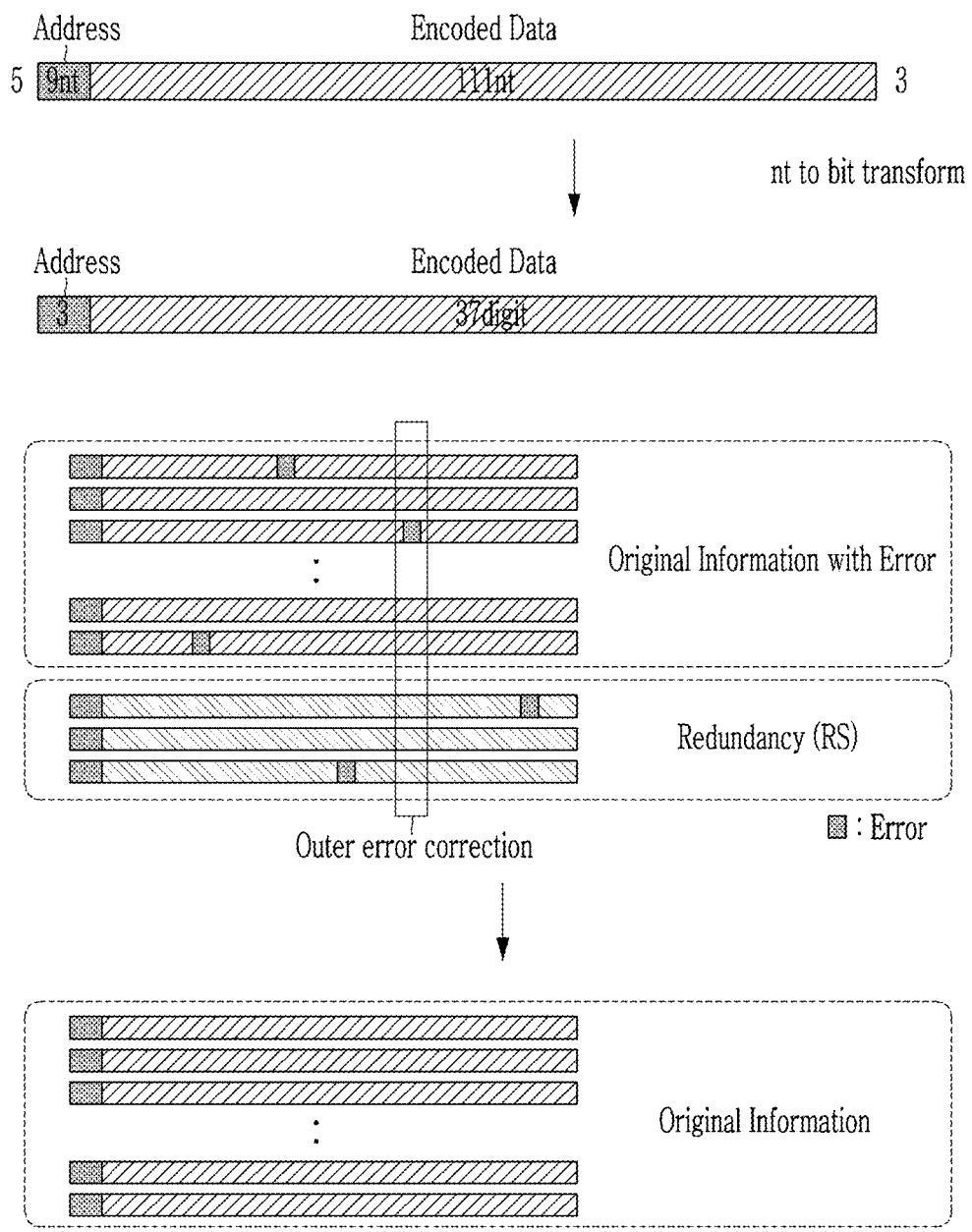
FIG. 5 is a diagram illustrating a data fragment structure (without an adapter) and an error correction system in a second experimental example.

FIG. 5 is a diagram illustrating a data fragment structure (without an adapter) and an error correction system in a second experimental example.

As illustrated in FIG. 5, Reed-Solomon based redundancy is added to cope with errors and amplification biases that may occur when synthesizing and amplifying oligonucleotide pools with high complexity.

In the exemplary embodiment illustrated in FIG. 5, degenerate bases 'W' and 'S' are added to encode the data. Table 3 is a codon table containing the degenerate bases W and S.

TABLE 3

| Data | Codon |
|---|---|
| 1 | ACA |
| 2 | CCA |
| 3 | TCA |
| 4 | GCA |
| 5 | WCA |
| 6 | SCA |
| 7 | ATA |
| 8 | CTA |
| 9 | TTA |
| 10 | GTA |
| 11 | WTA |
| 12 | STA |
| 13 | AGA |
| 14 | CGA |
| 15 | TGA |
| 16 | GGA |
| 17 | WGA |
| 18 | SGA |
| 19 | ASA |
| 20 | CSA |
| 21 | TSA |
| 22 | GSA |
| 23 | WSA |
| 24 | SSA |
| 25 | AAC |
| 26 | CAC |
| 27 | TAC |
| 28 | GAC |
| 29 | WAC |
| 30 | SAC |
| 31 | ATC |
| 32 | CTC |
| 33 | TTC |
| 34 | GTC |
| 35 | WTC |
| 36 | STC |
| 37 | AGC |
| 38 | CGC |
| 39 | TGC |
| 40 | GGC |
| 41 | WGC |
| 42 | SGC |
| 43 | AWC |
| 44 | CWC |

TABLE 3-continued

| Data | Codon |
|---|---|
| 45 | TWC |
| 46 | GWC |
| 47 | WWC |
| 48 | SWC |
| 49 | AAT |
| 50 | CAT |
| 51 | TAT |
| 52 | GAT |
| 53 | WAT |
| 54 | SAT |
| 55 | ACT |
| 56 | CCT |
| 57 | TCT |
| 58 | GCT |
| 59 | WCT |
| 60 | SCT |
| 61 | AGT |
| 62 | CGT |
| 63 | TGT |
| 64 | GGT |
| 65 | WGT |
| 66 | SGT |
| 67 | AST |
| 68 | CST |
| 69 | TST |
| 70 | GST |
| 71 | WST |
| 72 | SST |
| 73 | AAG |
| 74 | CAG |
| 75 | TAG |
| 76 | GAG |
| 77 | WAG |
| 78 | SAG |
| 79 | ACG |
| 80 | CCG |
| 81 | TCG |
| 82 | GCG |
| 83 | WCG |
| 84 | SCG |
| 85 | ATG |
| 86 | CTG |
| 87 | TTG |
| 88 | GTG |
| 89 | WTG |
| 90 | STG |
| 91 | AWG |
| 92 | CWG |
| 93 | TWG |
| 94 | GWG |
| 95 | WWG |
| 96 | SWG |
| 97 | ACW |
| 98 | CCW |
| 99 | TCW |
| 100 | GCW |
| 101 | WCW |
| 102 | SCW |
| 103 | AGW |
| 104 | CGW |
| 105 | TGW |
| 106 | GGW |
| 107 | WGW |
| 108 | SGW |
| 109 | ASW |
| 110 | CSW |
| 111 | TSW |
| 112 | GSW |
| 113 | WSW |
| 114 | SSW |
| 115 | AAS |
| 116 | CAS |
| 117 | TAS |
| 118 | GAS |
| 119 | WAS |
| 120 | SAS |
| 121 | ATS |
| 122 | CTS |

TABLE 3-continued

| Data | Codon |
|---|---|
| 123 | TTS |
| 124 | GTS |
| 125 | WTS |
| 126 | STS |
| 127 | AWS |
| 128 | CWS |

As illustrated in FIG. 5, encoded data 111 nt is decoded into 37-bit digital data based on the codon in Table 3. For example, when decoded original information has the error, the error is corrected based on redundancy (RS), so that the original information may be recovered without the error.

Even in the second experimental example, similarly as in the first experimental example, the result of randomly down-sampling the 250× coverage in the raw NGS data is repeated ten times. As a result, the raw data is recovered without the error in average coverage to 250× to achieve an information capacity of 2.0 bits/nt.

The platforms in the first and second experimental examples may be more specifically analyzed and compared with the platforms by Erlich and Zielinski in terms of a net information capacity, input data, the number of oligos, minimum coverage, and a physical density.

Table 4 shows the comparison between the first and second experimental examples and Erlich and Zielinski in terms of the net information capacity (bi/nt), the size of the input data, a full recovery status, and the number of oligos, the minimum NGS coverage (average), and the physical density (Pbytes/g).

TABLE 4

|  | Erlich and Zielinski | This work | |
|---|---|---|---|
| Net Information capacity (bit/nt) | 1.57 | 2 | 3.37 |
| Input data | 2.15 Mbyte | 135.4 Kbyte | 854 byte |
| Full recovery | Yes | Yes | Yes |
| Number of oligos | 72,000 | 4503 | 45 |
| Minimum NGS coverage (average) | 10x | 250x | 200x |
| Physical density (Pbytes/g) | 214 | 772 | 485 |

Although multiple oligonucleotide variants are synthesized in a single design fragment, the numbers of oligonucleotide molecules per design required for data recovery in the first and second experimental examples, respectively are 438 and 800. This is one of the improvements compared to the use of 1300 oligonucleotide molecules in data decoding in Erlich and Zielinski in the related art.

In addition, it can be seen that the net information capacity and the physical density, which are proven in first and second experiments, are also improved as compared with Erlich and Zielinski in the related art. The net information capacity is defined as the number of bits that may be stored per nucleotide (nt), and the physical density represents the size (Pbyte) of data which may be stored per unit weight (g) based on the calculated number of molecules by experimentally calculating the same number of molecules required for recovering the data.

As described above, when various types of degenerate bases are used on a large scale based on the data based on the first and second experiments, a possibility of the data recovery is simulated.

Figure 6A:
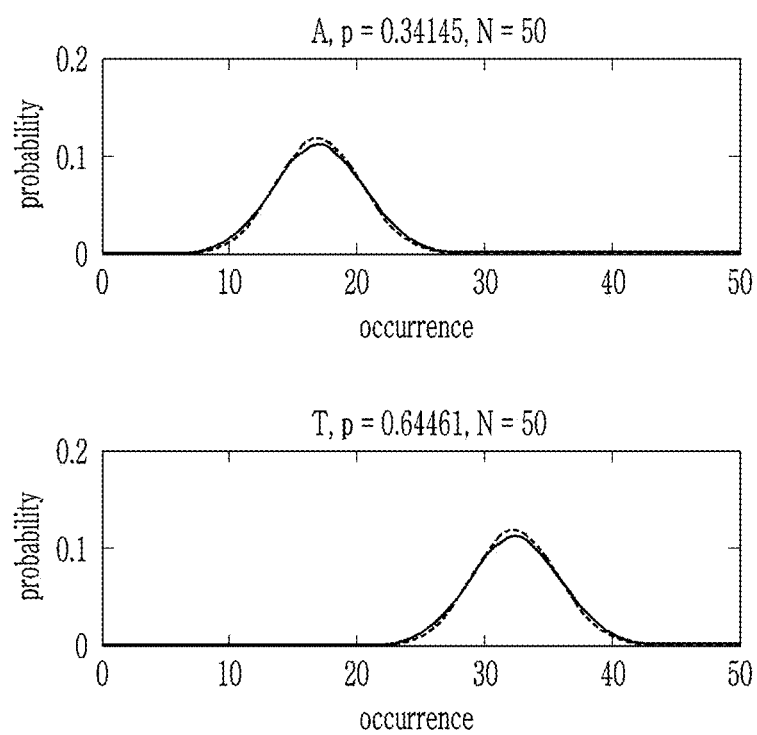
FIGS. 6A and 6B are graphs showing a call frequency of each base in a degenerate base.
Figure 6B:
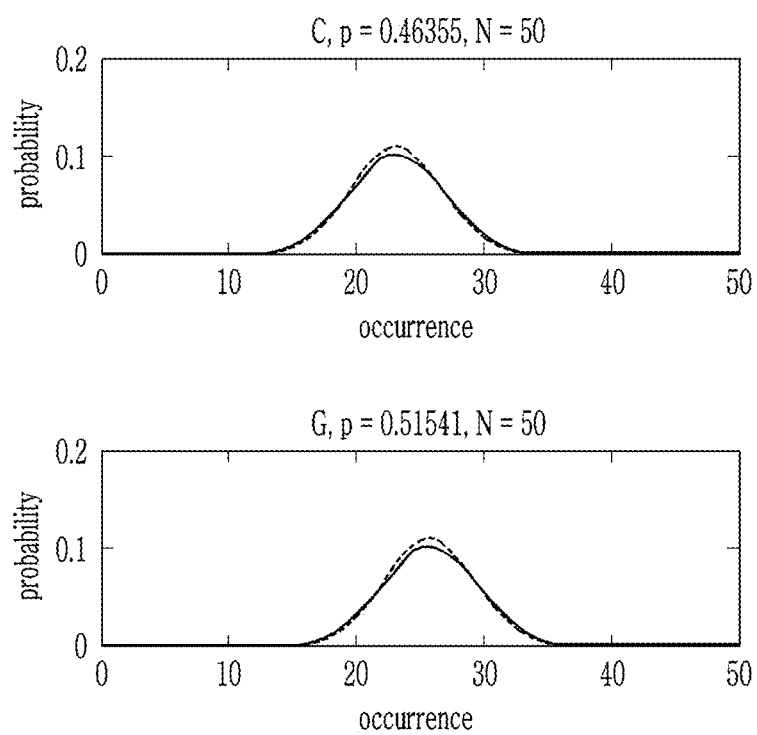

FIGS. 6A and 6B are graphs showing a call frequency of each base in a degenerate base.

Even when the bases A and T are mixed in the same ratio to encode the degenerate base W, call ratios in decoding are not the same. As illustrated in FIG. 6A, for 50 degenerate bases W, the call ratio of the base A is 0.34145, the call ratio of the base T is 0.64461, and the call frequency of each of the bases A and T follows a binomial distribution.

Similarly, even when the bases C and G are mixed in the same ratio to encode the degenerate base S, the call ratios in decoding are not the same. As illustrated in FIG. 6B, for 50 degenerate bases S, the call ratio of the base C is 0.46355, the call ratio of the base G is 0.51541, and the call frequency of each of the bases C and G follows the binomial distribution.

Since the call frequency of each base included in each degenerate base also follows the binomial distribution, the platform according to the exemplary embodiment may be modeled via a Monte-Carlo simulation. The Monte-Carlo simulation is a general modeling technique for generating and checking variables from a calculated probabilistic distribution computationally, when the probabilistic distribution is calculated.

A process modeled through the Monte-Carlo simulation may include repetition of operations 1 to 3 of 1) generating random data encoded including the degenerate base, 2) generating a base call distribution for the random data based on the binomial distribution, and 3) generating an error rate between the generated base call distribution and an actual base call distribution (or checking whether the data may be recovered), based on an assumption that the frequency follows a specific probabilistic distribution (binomial distribution).

Figure 7A:
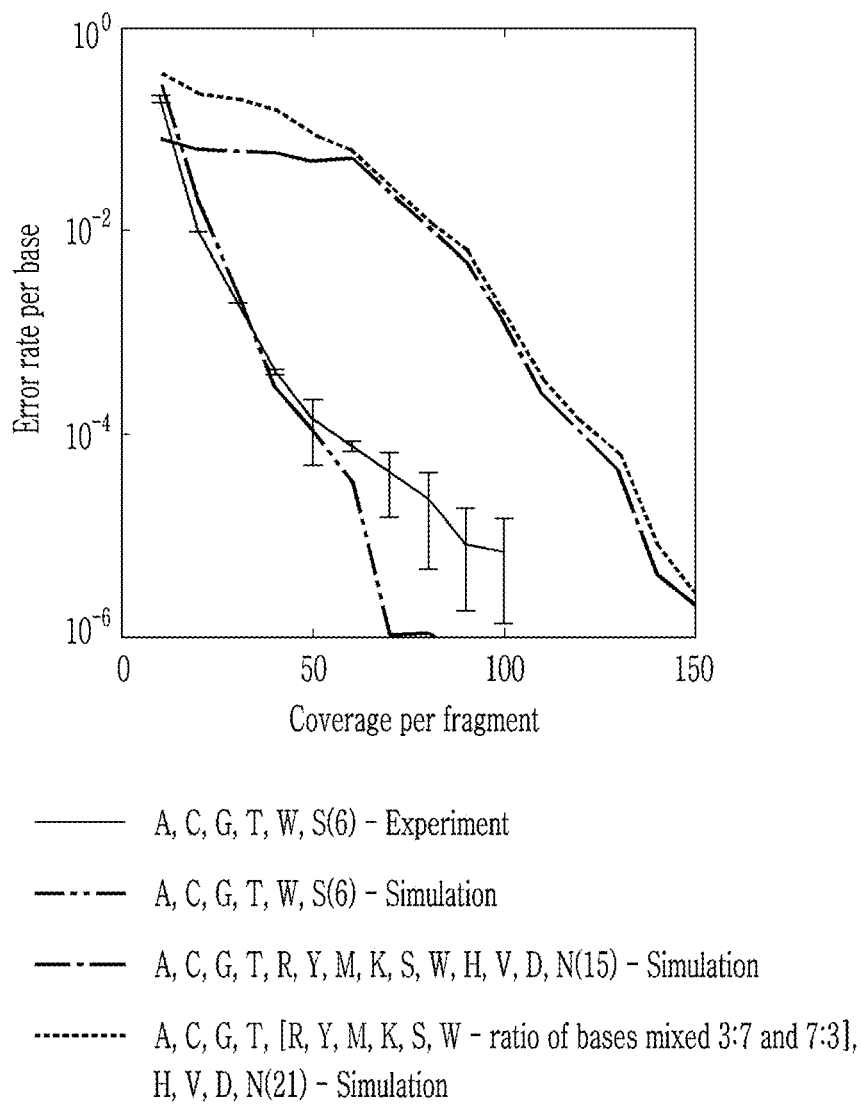
FIGS. 7A to 7C are graphs showing robustness and scalability of a platform according to the exemplary embodiment through experimental examples and simulation examples.
Figure 7B:
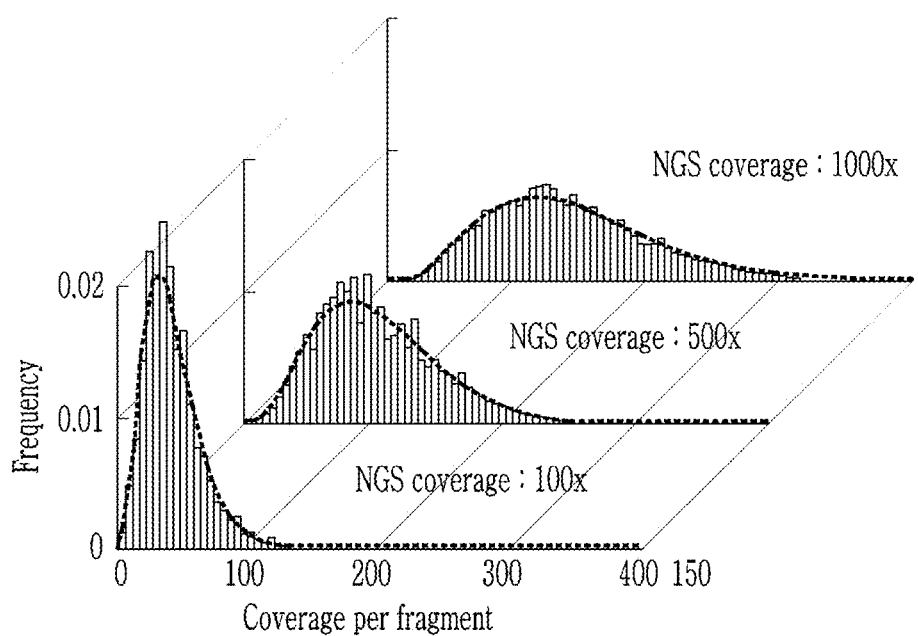
Figure 7C:
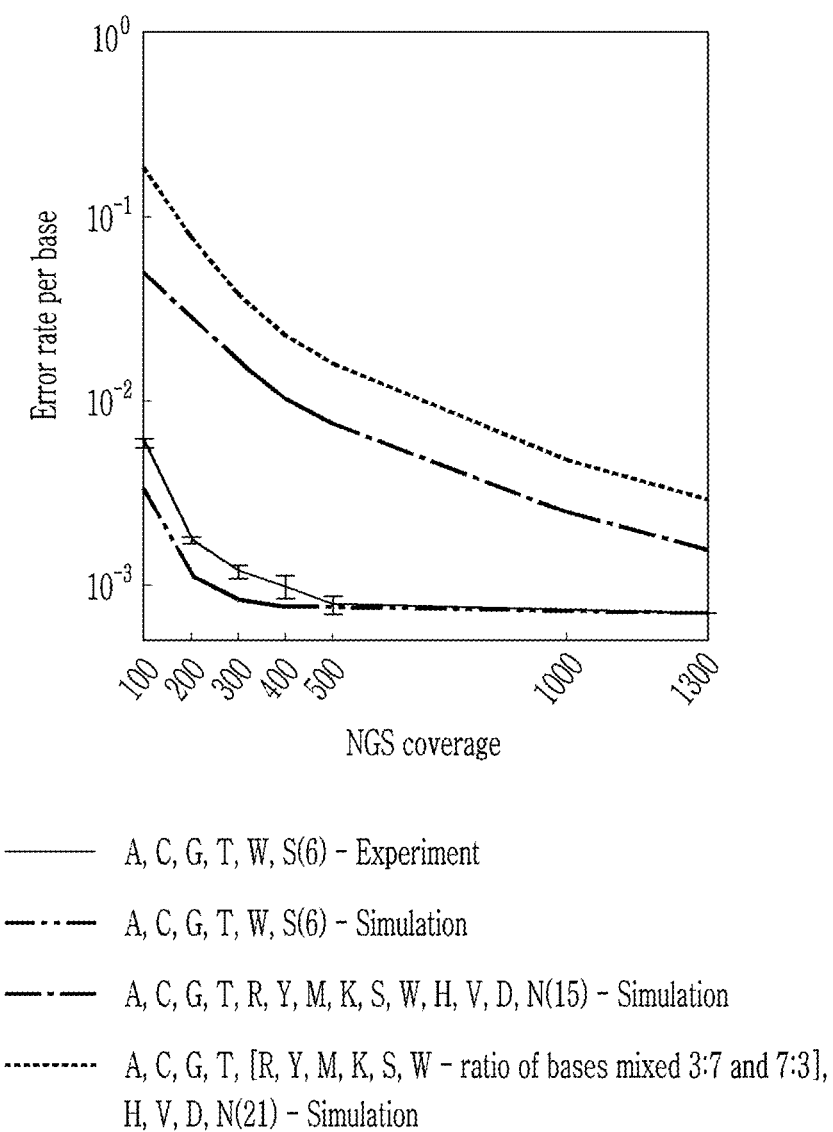

FIGS. 7A to 7C are graphs showing robustness and scalability of a platform according to the exemplary embodiment through experimental example and simulation examples.

FIG. 7A is a graph showing the error rate per base pair according to read coverage of the fragment. The graph of FIG. 7A may be based on a result of randomly and uniformly generating reads or sampling for experimental data.

In FIG. 7A, the error rate per base is shown according to the number of coverages per fragment. In this case, the error rate may be calculated by averaging the error rates of the bases. As illustrated in FIG. 7A, it can be seen in the experimental examples and the simulation examples that the error rate per base decreases as the number of coverage per fragment increases.

The result of the experimental example containing two degenerate bases W and S and the result of the simulation containing two degenerate bases W and S show a similar pattern. Therefore, based on the simulation result for the data encoded with 15 characters including the degenerate bases R, Y, M, K, S, W, H, B, V, D, and N, it may be predicted that a similar result may be derived even in the experimental example.

Further, based on the simulation result for the data encoded with 21 characters including 12 degenerate bases and 4 degenerate bases H, B, V, D, and N, it may be predicted that the similar result may be derived even in the experimental example. Each of 12 degenerate bases may be generated by varying the mixing ratio of the mixed bases. For example, each of the degenerate bases R, Y, M, K, S, and W may include a degenerate base in which the mixing ratio of the bases is 3:7 and a degenerate base in which the mixing ratio is 7:3. Specifically, W1 is designated for A:T=3:7 and W2 may be designated for A:T=7:3.

FIG. 7B is a graph showing the frequency with which the fragment is called by PCR bias through the experiment. As illustrated in FIG. 7B, the call frequency of the fragment represents an uneven profile. In FIG. 7B, the call frequency of the fragment read according to the number of NGS coverage times is illustrated. For example, call frequency distributions of fragments when the numbers of NGS coverage times are 100×, 500×, and 1000× are illustrated. That is, every time the NGS coverage is executed, not all fragments are read and fragments that are not read are generated. Further, even though the number of NGS coverage times increases, the call frequency distribution of the fragment is not improved. In FIG. 7B, a red line represents a negative binomial fit.

FIG. 7C illustrate the error rate per base pair according to the number of NGS coverage times for all fragments when applying that the frequency of calling the fragment is not even. In the graph of FIG. 7C, the standard deviation (s.d.) of an experimental result is obtained by repeating random sampling five times and the error bar indicates s.d.

By applying the call frequency according to the coverage of the fragment illustrated in FIG. 7B to the base error rate per coverage of the fragment illustrated in FIG. 7A, the error rate per base according to the number of NGS coverage times for all fragments illustrated in FIG. 7C may be simulated.

When various types of degenerate bases are used, the error rate increases, but the error rate decreases as the NGS coverage increases. When NGS coverage of 1300× or more is given in the simulation, information of 100 megabytes having 10% Reed-Solomon redundancy may be perfectly decoded.

In the simulation, it can be seen that the net information capacity and physical density of the NA digital data storage system which is previously reported may be experimentally doubled using the degenerate bases. The simulation also shows the scalability of the platform. Although the introduced platform requires a large amount of NGS, a sequencing technique is higher in evolution speed and a current DNA sequencing price is approximately 50,000 times lower than a synthesis price per base used the DNA digital data storage. From this, even if the platform according to the exemplary embodiment uses the NGS coverage of 2000×, sequencing cost is only 4% of the synthesis cost. The exemplary embodiment may provide the information capacity of the DNA digital data storage device that is at least twice as high as the information capacity of the previous report (Erlich and Zielinski).

Figure 8:
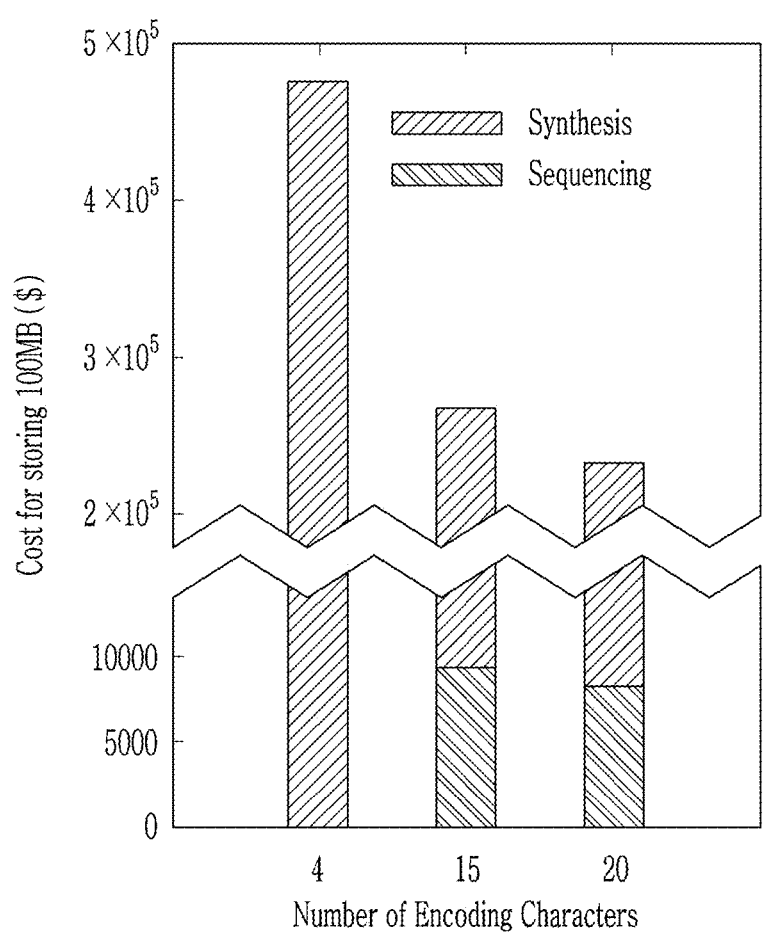
FIG. 8 is a graph showing a comparison of cost according to the exemplary embodiment with the cost in the related art.

FIG. 8 is a graph showing a comparison of cost according to the exemplary embodiment with the cost in the related art.

In FIG. 8, the cost for four encoding characters is calculated based on set-up of Erlich and Zielinski and the cost when the number of encoding characters according to the exemplary embodiment is 15 and 20 is cost when it is designed that the length of the fragment is 200 nt, the length of the address is 12 nt, the adapter is attached to both ends with 20 nt, and 10% Reed-Solomon error correction is inserted according to a set-up length of Erlich and Zielinski.

As illustrated in FIG. 8, even when a DNA sequencing price is increased as compared with the price in the related art, the pool-based oligonucleotide synthesizer may reduce the DNA digital data storage cost by half or more when synthesizing the degenerate bases.

The exemplary embodiment shows that the net information capacity and physical density of the DNA-based data storage system previously reported may be experimentally doubled using degenerate bases. The scalability and cost competitiveness of the platform based on the exemplary embodiment is proved through the simulation. The exemplary embodiment may be used for column-based oligonucleotide pool synthesis setup where all degenerate bases may be used. The synthesis setup needs to precisely control the ratio of the nucleotides with a low deviation of the nucleotide combination. Then, by optimizing the platform in a large-scale experiment, modulated degenerate bases using non-equivalent ratios suggested in the simulation may be used.

Further, when synthesis and sequencing methods for the synthetic bases are developed, the modulated degenerate bases may be used with other types of additional encoding characters. In the first and second experimental examples, the degenerate base is composed of a mixture of at least two bases of DNA bases A, T, G, and C, but the invention is not limited thereto. For example, a chemical synthesis method is known for RNA bases or nucleic acid analogues (https://en.wikipedia.org/wiki/Nucleic_acid_analogue) including PNA, XNA, ZNA, etc. in addition to the DNA and it is known that the RNA bases or the nucleic acid analogues may be amplified with an enzyme known in the related art or a modification thereof. Therefore, with the development of the sequencing methods therefor, the RNA bases or the nucleic acid analogues may be used as degenerate bases corresponding to other types of encoding characters.

International Patent Publication No. WO 2017/011492 A1 discloses that the RNA other than the DNA and nucleic acid analogues including Z, P, dNaM, dSSIC, isoC, isoG, Ds, Px, peptide nucleic acid (PNA), Xeno nucleic acid (XNA), Zip nucleic acid (ZNA), and the like may be amplified by using chemical synthesis and polymerase. The nucleic acid analogue refers to biochemicals that are similar in structure to the DNA and the RNA, but in which a backbone is not a phosphate backbone or the structure of the base is different from A, G, T, C, and U.

The degenerate base according to the exemplary embodiment may be defined as a mixture of at least two of DNA, RNA, and the nucleic acid analogs, and the encoding character corresponding to the degenerate base may be used for data storage. Molecular structures of the DNA bases, the RNA bases, and the nucleic acid analogs, respectively and a base pairing molecular structure are described below.

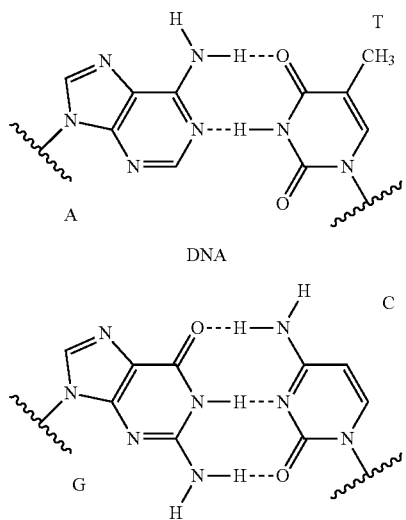

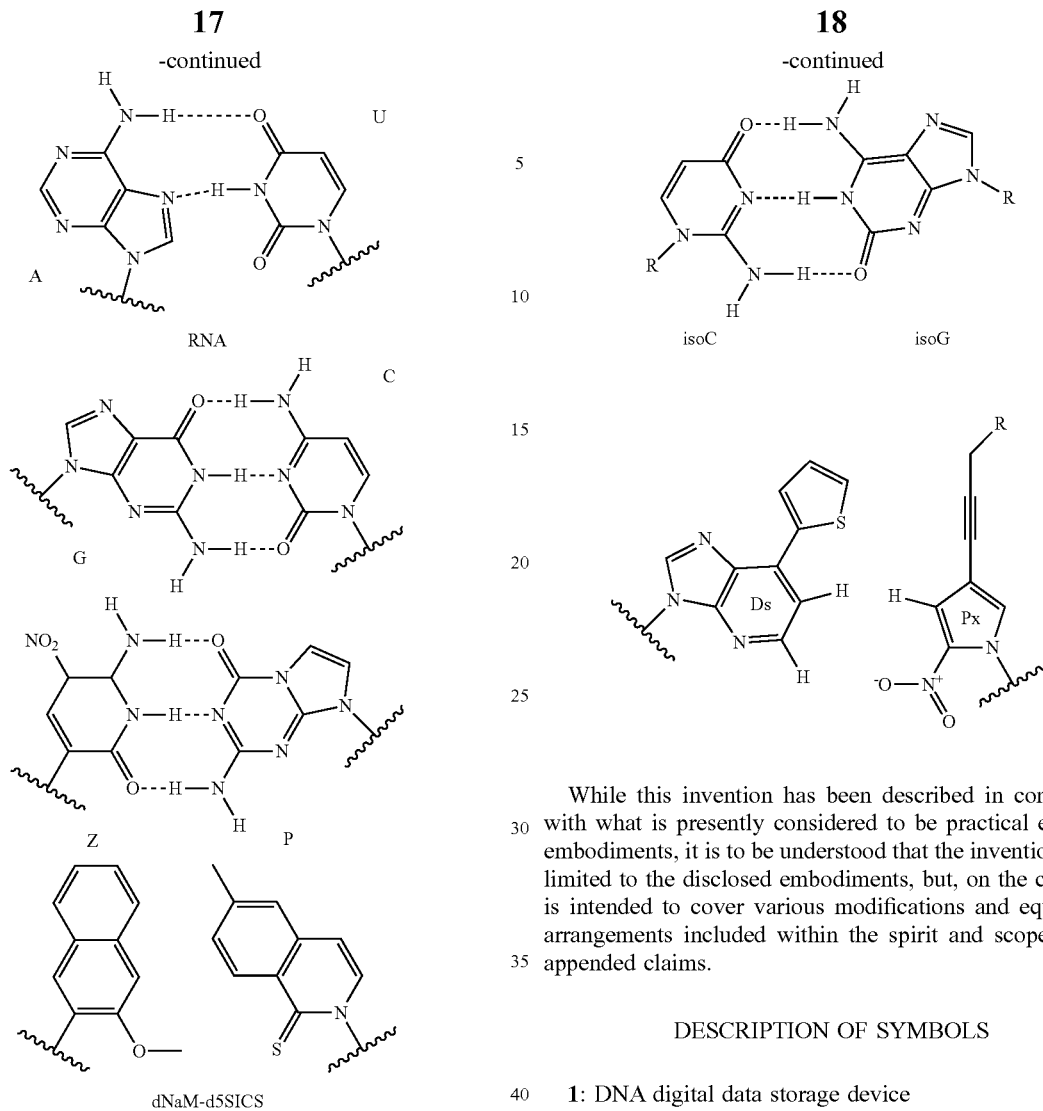

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

1: DNA digital data storage device
11: Memory cell

What is claimed is:

1. A generation method of DNA digital data, the method comprising:
   encoding a plurality of bit data into a plurality of DNA base sequences including at least one degenerate base; and
   synthesizing at least two types of bases constituting the at least one degenerate base based on a mixing ratio.

2. The generation method of claim 1, further comprising:
   synthesizing a single type of base among the plurality of base sequences.

3. The method of claim 1, wherein:
   the synthesizing of the at least one degenerate base includes,
   incorporating the at least two types of bases based on the mixing ratio.

4. The generation method of claim 1, wherein:
   the synthesizing of the at least one degenerate base includes,
   incorporating the at least two types of bases mixed according to the mixing ratio on the outside.

5. The generation method of claim 1, wherein:
   the ratios of the at least two types of bases are the same in the mixing ratio.

6. The generation method of claim 1, wherein:
   the ratios of the at least two types of bases are different in the mixing ratio.

7. The generation method of claim 1, wherein:
   the at least two types of bases are at least one of a DNA base, an RNA base, and a nucleic acid analogue.

8. Device for storing data in DNA in which a plurality of base sequences to which a plurality of bit data is encoded is divided and stored as a basic storage unit, the device comprising:
   a plurality of storage units storing molecules in which a plurality of bases is synthesized based on a base sequence corresponding to the basic storage unit among the plurality of base sequences,
   wherein the base sequence includes a first degenerate base consisting of at least two types of bases, and
   the molecules include
   first molecules in which a base is synthesized among the at least two types of bases, and
   second molecules in which at least another base is synthesized among the at least two types of bases.

9. The storage device of claim 8, wherein:
   ratios between the first molecules and the second molecules follow a mixing ratio.

10. The storage device of claim 9, wherein:
    the ratios of the at least two types of bases are the same in the mixing ratio.

11. The storage device of claim 9, wherein:
    the ratios of the at least two types of bases are different in the mixing ratio.

12. The storage device of claim 8, wherein:
    the at least two types of bases are at least one of a DNA base, an RNA base, and a nucleic acid analogue.

13. A decoding method of DNA data, comprising:
    categorizing a plurality of DNA fragments according to an address;
    analyzing a base at the same position with respect to each of the plurality of categorized DNA fragments;
    calculating a scatter plot of a base ratio based on a result of the analysis;
    determining a base at a corresponding location as a degenerate base when the scatter plot of the base ratio is a mixing ratio of at least two bases; and
    decoding data based on the determined degenerated base.

14. The decoding method of claim 13, wherein:
    the analyzing of the base includes,
    analyzing a base call for each location of each of the plurality of DNA fragments.

15. The decoding method of claim 13, wherein:
    the base at the corresponding location is determined as a first degenerate base when the scatter plot of the base ratio is a first mixing ratio of at least two bases,
    the base at the corresponding location is determined as a second degenerate base when the scatter plot of the base ratio is a second mixing ratio of the at least two bases, and
    the first mixing ratio and the second mixing ratio are different from each other and the first degenerate base and the second degenerate base are different from each other.

* * * * *